United States Patent
Frey et al.

(10) Patent No.: US 9,883,888 B2
(45) Date of Patent: Feb. 6, 2018

(54) SENSOR CARTRIDGE AND INSERTER

(71) Applicant: Roche Diagnostics Operations, Inc., Indianapolis, IN (US)

(72) Inventors: Stephan-Michael Frey, Griesheim (DE); Wolfgang Heck, Frankenthal (DE); Oliver Kube, Worms (DE); Helmut Walter, Heppenheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 379 days.

(21) Appl. No.: 14/554,304

(22) Filed: Nov. 26, 2014

(65) Prior Publication Data
US 2015/0080690 A1 Mar. 19, 2015

Related U.S. Application Data

(63) Continuation of application No. PCT/EP2013/060364, filed on May 21, 2013.

(30) Foreign Application Priority Data

May 31, 2012 (EP) .................................... 12170224

(51) Int. Cl.
*A61B 5/1473* (2006.01)
*A61B 5/1486* (2006.01)
(Continued)

(52) U.S. Cl.
CPC ........ *A61B 17/3468* (2013.01); *A61B 5/1473* (2013.01); *A61B 5/14532* (2013.01);
(Continued)

(58) Field of Classification Search
CPC ............ A61B 17/3468; A61B 5/14532; A61B 5/14542; A61B 5/14546; A61B 5/1473;
(Continued)

(56) References Cited

U.S. PATENT DOCUMENTS 5,390,671 A 2/1995 Lord et al.
7,310,544 B2 * 12/2007 Brister ................. A61B 5/0002
600/345
(Continued)

FOREIGN PATENT DOCUMENTS

CN 101801791 A 8/2010
CN 102368954 A 3/2012
(Continued)

OTHER PUBLICATIONS

International Search Report, PCT/EP2013/060364, dated Oct. 4, 2013.
(Continued)

*Primary Examiner* — Navin Natnithithadha
(74) *Attorney, Agent, or Firm* — Bose McKinney & Evans LLP

(57) ABSTRACT

A sensor cartridge comprising a sterile capsule. The sensor cartridge further comprises a sensor within the sterile capsule. The sensor cartridge further comprises a sensor connector connected to the sensor in an initial position. The sensor cartridge further comprises an insertion needle for inserting the sensor into a subject. The insertion needle is within the sterile capsule. The sensor cartridge further comprises a sensor mounting unit for receiving the sensor connector at a mounted position. The sensor mounting unit comprises an adhesive surface for attaching to an exterior surface of the subject. The sensor cartridge further comprises an insertion mechanism operable for actuating the insertion needle and moving the sensor connector from the initial position to the mounted position.

9 Claims, 9 Drawing Sheets

(51) Int. Cl.
*A61B 17/34* (2006.01)
*A61B 5/00* (2006.01)
*A61B 5/145* (2006.01)
*A61B 5/15* (2006.01)
*A61B 5/151* (2006.01)

(52) U.S. Cl.
CPC ...... *A61B 5/14542* (2013.01); *A61B 5/14546* (2013.01); *A61B 5/14865* (2013.01); *A61B 5/686* (2013.01); *A61B 5/6849* (2013.01); *A61B 5/15003* (2013.01); *A61B 5/15016* (2013.01); *A61B 5/15142* (2013.01); *A61B 5/150221* (2013.01); *A61B 5/150305* (2013.01); *A61B 5/150633* (2013.01); *A61B 5/150992* (2013.01)

(58) Field of Classification Search
CPC ............ A61B 5/14865; A61B 5/15003; A61B 5/15016; A61B 5/150221; A61B 5/150305; A61B 5/150633; A61B 5/150992; A61B 5/15142; A61B 5/6849; A61B 5/686
USPC .......................................... 600/309, 345–366
See application file for complete search history.

(56) References Cited

U.S. PATENT DOCUMENTS

| | | | | |
|---|---|---|---|---|
| 7,381,184 B2* | 6/2008 | Funderburk | ....... | A61B 5/14532 600/300 |
| 7,582,059 B2* | 9/2009 | Funderburk | ....... | A61B 5/14532 600/309 |
| 7,697,967 B2* | 4/2010 | Stafford | ............. | A61B 5/14503 600/345 |
| 7,883,464 B2* | 2/2011 | Stafford | ............. | A61B 5/14532 600/309 |
| 7,946,984 B2* | 5/2011 | Brister | ................ | A61B 5/0002 600/347 |
| 8,002,752 B2 | 8/2011 | Yodfat et al. | | |
| 8,029,442 B2* | 10/2011 | Funderburk | ....... | A61B 5/14532 600/300 |
| 8,229,534 B2* | 7/2012 | Brister | ................ | A61B 5/0002 600/309 |
| 8,545,403 B2* | 10/2013 | Peyser | ............... | A61B 5/14532 600/365 |
| 8,852,101 B2* | 10/2014 | Stafford | ............. | A61B 5/14503 600/309 |
| 9,078,626 B2* | 7/2015 | Brister | ................ | A61B 5/0002 |
| 9,295,786 B2* | 3/2016 | Gottlieb | ............... | A61B 5/6849 |
| 2004/0133164 A1* | 7/2004 | Funderburk | ....... | A61B 5/14532 604/134 |
| 2006/0142651 A1 | 6/2006 | Brister et al. | | |
| 2007/0078320 A1* | 4/2007 | Stafford | ............. | A61B 5/14532 600/347 |
| 2007/0249922 A1* | 10/2007 | Peyser | ............... | A61B 5/14532 600/365 |
| 2008/0004512 A1* | 1/2008 | Funderburk | ....... | A61B 5/14532 600/309 |
| 2008/0033268 A1* | 2/2008 | Stafford | ............. | A61B 5/14503 600/345 |
| 2008/0064941 A1* | 3/2008 | Funderburk | ....... | A61B 5/14532 600/347 |
| 2008/0114280 A1* | 5/2008 | Stafford | ............. | A61B 5/14532 604/19 |
| 2008/0242962 A1 | 10/2008 | Roesicke et al. | | |
| 2009/0292184 A1* | 11/2009 | Funderburk | ....... | A61B 5/14532 600/309 |
| 2009/0292185 A1* | 11/2009 | Funderburk | ....... | A61B 5/14532 600/309 |
| 2009/0299301 A1* | 12/2009 | Gottlieb | ............... | A61B 5/6849 604/263 |
| 2010/0222799 A1 | 9/2010 | Roeper et al. | | |
| 2010/0241030 A1 | 9/2010 | Fowler et al. | | |
| 2010/0331646 A1* | 12/2010 | Hoss | .................. | A61B 5/14503 600/347 |
| 2011/0021889 A1 | 1/2011 | Hoss et al. | | |
| 2011/0144464 A1* | 6/2011 | Stafford | ............. | A61B 5/14532 600/347 |
| 2011/0190603 A1* | 8/2011 | Stafford | ............. | A61B 5/14532 600/309 |

FOREIGN PATENT DOCUMENTS

DE 10 2008 053 216 A1 5/2010
WO WO 2008/065646 A1 6/2008

OTHER PUBLICATIONS

International Preliminary Report on Patentability and Written Opinion of the International Searching Authority, PCT/EP2013/060364, dated Aug. 8, 2014.

* cited by examiner

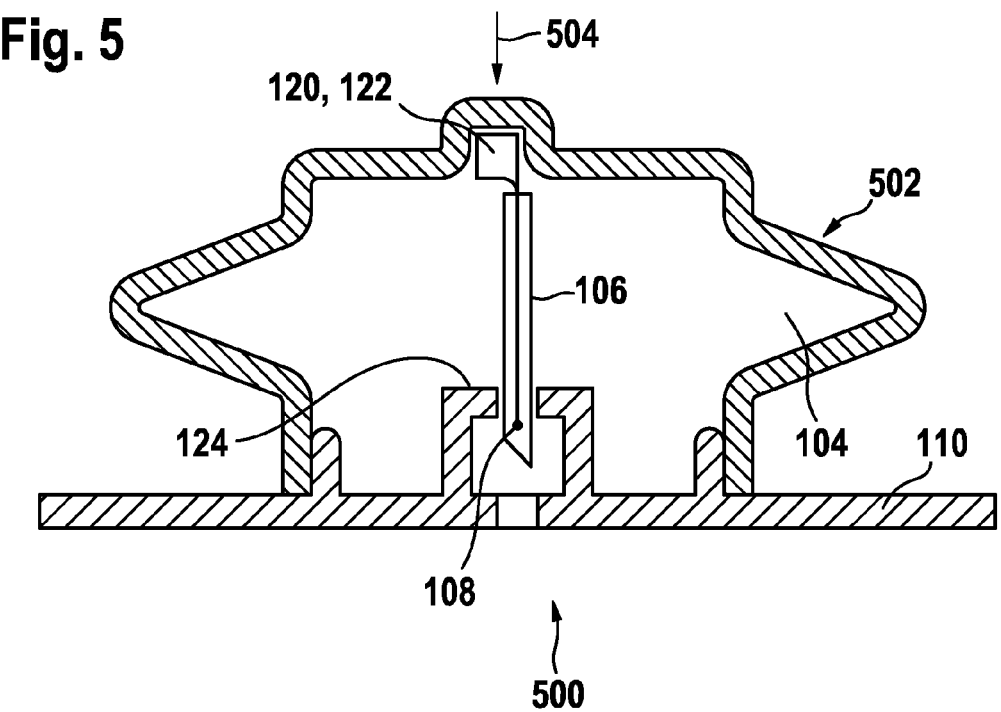
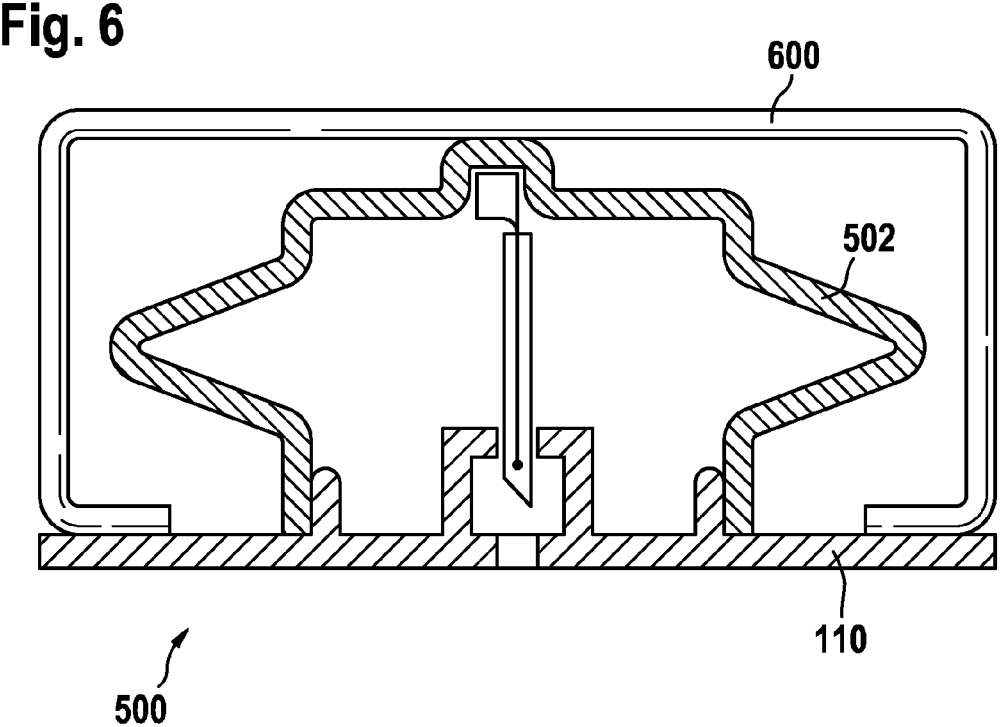

SENSOR CARTRIDGE AND INSERTER

RELATED APPLICATIONS

This application is a continuation of PCT/EP2013/060364, filed May 21, 2013, which claims priority to EP 12170224.5, filed May 31, 2012, both of which are hereby incorporated herein by reference in their entireties.

BACKGROUND

The invention relates to sensors for in vivo monitoring of an analyte, in particular to devices for inserting a sensor into a subject.

For the proper management of chronic health conditions it may be crucial for a subject to periodically monitor one or more analyte levels in his or her blood stream. In the case of diabetes the subject routinely monitors the glucose levels to avoid hypoglycemic episodes and hyperglycemic episodes. For other situations where health monitoring is important, other analytes, such as lactate or oxygen, may be measured.

A typical means of performing such monitoring is the repeated drawing of blood by the subject to provide a sample for analysis by a monitoring system. This provides a cost effective way monitoring chronic diseases such as diabetes, but it may be inconvenient and only provides data on the analyte concentration at the time intervals when the test was performed.

Systems have also been developed which allow a sensor to be implanted into a subject to monitor the analyte concentration directly within the bloodstream or within the interstitial fluids. For instance, an electrochemical sensor may be inserted into a subcutaneous region of the subject where the analyte concentration is continuously monitored and/or logged.

For instance, United States patent application US 2008/0242962 A1 discloses a monitoring system for monitoring analyte concentration, such as glucose, with an implantable sensor.

A disadvantage of current systems for inserting subcutaneous sensor systems is that the they may require that an inserter is used each time a sensor is inserted into a subject. A further disadvantage of current systems is that typically a large volume and amount of packaging is used.

SUMMARY

This disclosure teaches a sensor cartridge and an inserter. In one aspect, this disclosure provides for a sensor cartridge comprising a sterile capsule. The sensor cartridge further comprises a sensor within the sterile capsule. The sensor is located at an initial position within the sterile capsule. The sensor cartridge further comprises an insertion needle for inserting the sensor into a subject. The insertion needle is within the sterile capsule. The insertion needle may be a hollow needle with a cross-section that has been removed. For example, the needle may have a cross-section that resembles the letter "c."

The sensor cartridge further comprises a sensor mounting unit for receiving the sensor at a mounted position. The sensor mounting unit comprises an adhesive surface for attaching to an exterior surface of the subject. The sensor cartridge further comprises an insertion mechanism, or actuator, operable for actuating the insertion needle and moving the sensor from the initial position to the mounted position. This embodiment may be advantageous because the sensor, insertion needle and sensor mounting unit can all be incorporated into one package which may be provided with a sterile capsule. A subject or healthcare provider installing a sensor into a subject may simply adhere the sensor mounting unit to the exterior surface of the subject and then use the insertion mechanism to insert the sensor into the subject. The insertion needle moves the sensor into the subject and into the mounted position, the insertion needle then withdraws. In some embodiments the insertion needle is protected by what was previously the sterile capsule. This may eliminate the need for individual sharps disposal units. The insertion needle may be a hollow needle with a channel cut through it or a solid needle with a channel cut through it for accommodating the sensor. In some embodiments a cross-section of the needle has a C-shape to it.

In another aspect, this disclosure provides for a sensor cartridge comprising a sterile capsule. The sensor cartridge further comprises a sensor within the sterile capsule. The sensor cartridge further comprises a sensor connector connected to the sensor in an initial position. The sensor cartridge further comprises an insertion needle for inserting the sensor into a subject. The insertion needle is within the sterile capsule. The insertion needle may be a hollow needle with a cross-section that has been removed. For example, the needle may have a cross-section that resembles the letter "c." The sensor may be attached to or located within the insertion needle.

The sensor cartridge further comprises a sensor mounting unit for receiving the sensor connector at a mounted position. The sensor mounting unit comprises an adhesive surface for attaching to an exterior surface of the subject. The sensor cartridge further comprises an insertion mechanism operable for actuating the insertion needle and moving the sensor connector from the initial position to the mounted position. This embodiment may be advantageous because the sensor, insertion needle and sensor mounting unit can all be incorporated into one package which may be provided with a sterile capsule. A subject or healthcare provider installing a sensor into a subject may simply adhere the sensor mounting unit to the exterior surface of the subject and then use the insertion mechanism to insert the sensor into the subject. The insertion needle moves the sensor into the subject and the sensor connector into the mounted position, the insertion needle then withdraws. In some embodiments the insertion needle is protected by what was previously the sterile capsule. This may eliminate the need for individual sharps disposal units. The insertion needle may be a hollow needle with a channel cut through it or a solid needle with a channel cut through it for accommodating the sensor. In some embodiments a cross-section of the needle has a C-shape to it.

In another embodiment, the sensor cartridge further comprises a knob. The insertion mechanism is operable for actuating the insertion needle in a linear direction upon rotation of the knob. This embodiment may be beneficial because the knob forms a so called helper mechanism which is used for actuating the insertion mechanism. If a subject were to use the sensor cartridge for installing a sensor into his or herself it may be difficult for the subject to directly push the needle into his or herself. The rotation of the knob causes the insertion mechanism to linearly insert the insertion needle. However, because the knob is rotated in a different direction in a rotational fashion it is easier for the subject to perform the act. In some embodiments, the knob is rotated in only one direction. The rotation motion first inserts the needle and then withdraws it. In other embodiments the subject turns the needle in one direction to insert the needle. After insertion, the subject turns the knob in the opposite direction to withdraw the needle.

In one example, the sensor cartridge further comprises a bellows for providing the sterile capsule. The insertion mechanism comprises the bellows. The bellows are operable for being compressed by an operator or a subject. The insertion mechanism is operable for actuating the insertion needle upon compression of the bellows. Essentially the insertion mechanism may be operated by compressing or depressing the bellows. This embodiment may be beneficial because it provides a very simple mechanism which also provides the sterile capsule. Due to the lack of a further moving part it may reduce the cost of manufacturing using such a sensor cartridge. The bellows may also remove the insertion needle from the subject. When the bellows are no longer compressed they may spring back to their original form and withdraw the insertion needle in the process.

In another embodiment, the sensor mounting unit is detachable from the insertion mechanism. In other words the sensor mounting unit may be attached to the insertion mechanism and able to be removed from the insertion mechanism. The insertion mechanism is operable for detaching the sensor mounting unit from the insertion mechanism at a predetermined point in the actuation of the insertion needle. This embodiment may be beneficial because it allows the insertion mechanism to be removed from the sensor mounting unit. This may reduce the weight that the subject needs to carry when a sensor is installed into the subject.

In another embodiment, the insertion mechanism comprises a spring clip for attaching the sensor mounting unit to the insertion mechanism. The insertion mechanism may be operable for detaching the spring clip from the insertion mechanism or detaching the sensor mounting unit from the insertion mechanism. In other words the insertion mechanism is able for opening the spring clip to detach the sensor mounting unit from the insertion mechanism.

In another embodiment, the sensor cartridge further comprises a pressurized vessel for forming the sterile capsule. A pressure differential between the pressurized vessel and outside the sensor cartridge is operable for attaching the insertion mechanism to the mounting unit. The sensor cartridge further comprises a seal and/or valve for maintaining the pressure differential. The insertion mechanism is operable for causing the seal and/or valve to release the pressure differential during actuation of the insertion mechanism. This embodiment may be beneficial because the insertion mechanism is automatically detached from the sensor mounting unit when the pressure is released and also because the sterile capsule was formed by the pressurized vessel. When the pressurized vessel loses its pressure the sterile capsule may decrease in size. This reduces the amount of waste that needs to be disposed of.

In some examples of this embodiment, the insertion mechanism may cause or be operable to release the pressure differential at a predetermined point in the actuation of the insertion needle. This causes the insertion mechanism to detach from the sensor mounting unit.

In another embodiment, the sterile capsule is a hollow cavity. The insertion mechanism comprises a piston. The insertion mechanism is operable for pushing the piston into the hollow cavity for actuating the insertion mechanism for driving the insertion needle into the subject. The insertion mechanism is further operable for retracting the insertion needle back into the hollow cavity after insertion of the sensor into the subject using the piston. Bringing the insertion needle back into the hollow cavity may be advantageous, because the hollow cavity can contain and protect the insertion needle after use. This may eliminate the need for a separate sharps container.

In another example, the sterile capsule is sealed with a septum. The insertion mechanism is operable for pushing the insertion needle through the septum. The septum is operable for attaching to the sensor mounting unit. The use of a septum is advantageous because the needle can cross through the septum breaking out of the sterile capsule. The use of a septum may eliminate the need for removing a seal or sealing means from a sterile capsule.

In another example, the sensor cartridge further comprises a cover for covering the adhesive surface and for sealing the sterile compartment. For instance a portion of the insertion mechanism could be restrained by the cover or a portion of a linkage may not be able to move freely until the cover is removed. This embodiment may be advantageous because the removal of the cover of the adhesive surface enables the insertion needle to insert the sensor into the subject. and functions as a safety.

In another example, removal of the cover enables actuation of the insertion mechanism. This embodiment is advantageous because it may reduce or eliminate the actuation of the insertion mechanism when the sensor mounting unit is not attached to the exterior surface of a subject. This may for instance reduce the chances that the insertion mechanism will be actuated at the wrong time and inflict an injury on someone with the insertion needle.

In another example, the sensor cartridge further comprises a package for forming the sterile capsule. The cover forms at least a portion of the package. This embodiment may be advantageous because the cover forms part of the packaging of the sensor cartridge and the packaging forms the sterile capsule. This may reduce the amount of waste which needs to be discarded and may also reduce the manufacturing costs of the sensor cartridge.

In another embodiment, the insertion mechanism comprises a safety which is moveable from an operable to an inoperable position. The insertion mechanism prevents actuation of the needle when the safety is in the inoperable position and the mechanism is able to actuate the needle when the safety is in the operable position. This embodiment may be advantageous because it may prevent actuation of the insertion mechanism when it is not intended. This may for instance reduce the chance of accidental injury by the insertion needle.

In another embodiment, the insertion mechanism is operable to couple to a helper mechanism of an inserter. The helper mechanism is operable for actuating the insertion mechanism. The use of a helper mechanism may be beneficial because the helper mechanism may take work or action directed in a direction other than the direction that the insertion needle travels. This may make it easier for a subject to actuate the insertion mechanism his or herself.

In another embodiment, the sensor is an electrochemical sensor.

In another embodiment, the sensor is any one of the following: a glucose sensor, a lactate sensor, and an oxygen sensor.

In another embodiment, the insertion mechanism is further operable for retracting the insertion needle into the sterile capsule after actuating the insertion needle and moving the sensor from the initial position to the mounted position. This embodiment may be beneficial because the sterile capsule may provide protection to the used insertion needle. This may for instance reduce the need for a separate sharps container.

In another example, an inserter comprises a helper mechanism operable for coupling to an insertion mechanism of a sensor cartridge according to an embodiment of this disclosure. In some examples the inserter may be a re-usable inserter able to be re-loaded only with a new sensor cartridge or cartridges after use. This may enable the use of a reusable inserter for inserting single use sensors. The helper mechanism may prevent a used sensor cartridge from being used a second time.

In another example, the inserter is operable for puncturing a package of the sensor cartridge for forming the sterile capsule to couple to the insertion mechanism. This may be beneficial because puncturing of the package by the helper mechanism may do work that is necessary to prepare the sensor cartridge for use.

In another example, this disclosure provides for an inserter assembly comprising an inserter according to an embodiment of this disclosure and a sensor cartridge according to an embodiment of this disclosure.

It is understood that one or more of the aforementioned embodiments of this disclosure and/or examples may be combined as long as the combinations are not mutually exclusive.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 5 illustrates a sensor cartridge according to a further example;

FIG. 6 illustrates a safety which may be implemented on the sensor cartridge shown in FIG. 5;

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Like numbered elements in these figures are either equivalent elements or perform the same function. Elements which have been discussed previously will not necessarily be discussed in later figures if the function is equivalent.

Figure 1:
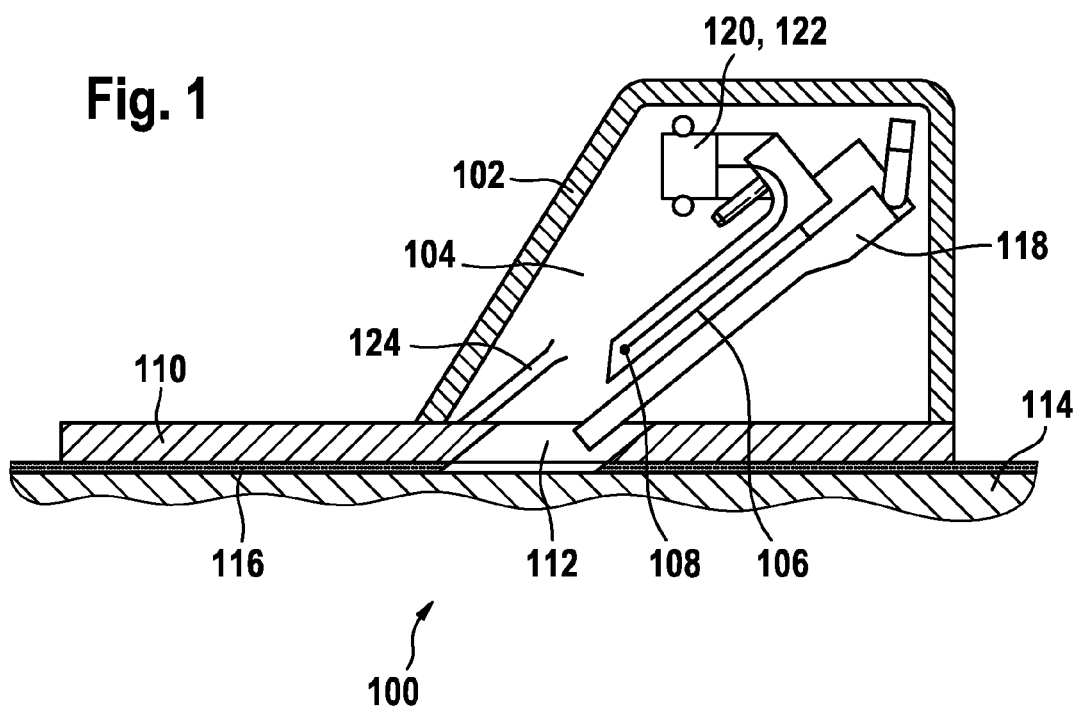
FIG. 1 illustrates an example of a sensor cartridge.

FIG. 1 shows an example of a sensor cartridge according to this disclosure. There is a package 102 which forms a sterile capsule 104. Within the sterile capsule 104 is an insertion needle 106. Also within the sterile capsule is a sensor 108 which is located within a cavity of the insertion needle 106. There is a sensor mounting unit 110 which forms a bottom portion of the sterile capsule 104. The sensor mounting unit 110 has a hole 112 through which the insertion needle 106 can be inserted into a subject 114. The sensor mounting unit 110 has an adhesive surface 116 in contact with the subject 114 for attaching the sensor mounting unit 110 to the subject 114. Also within the sterile capsule 104 is an insertion mechanism 118 for actuating the insertion needle 106. There is a sensor connector 120 mounted near the top of the insertion needle 106. The sensor connector 120 is connected to the sensor 108. When the insertion needle 106 is inserted into the subject 114 the sensor connector 120 is moved from an initial position 122 to a mounted position 124. In some examples the sensor connector 120 may lock into the mounted position 124. The insertion needle 106 then withdraws leaving the sensor 108 within the subject 114 and the sensor connector 120 in the mounted position 124.

Figure 2:
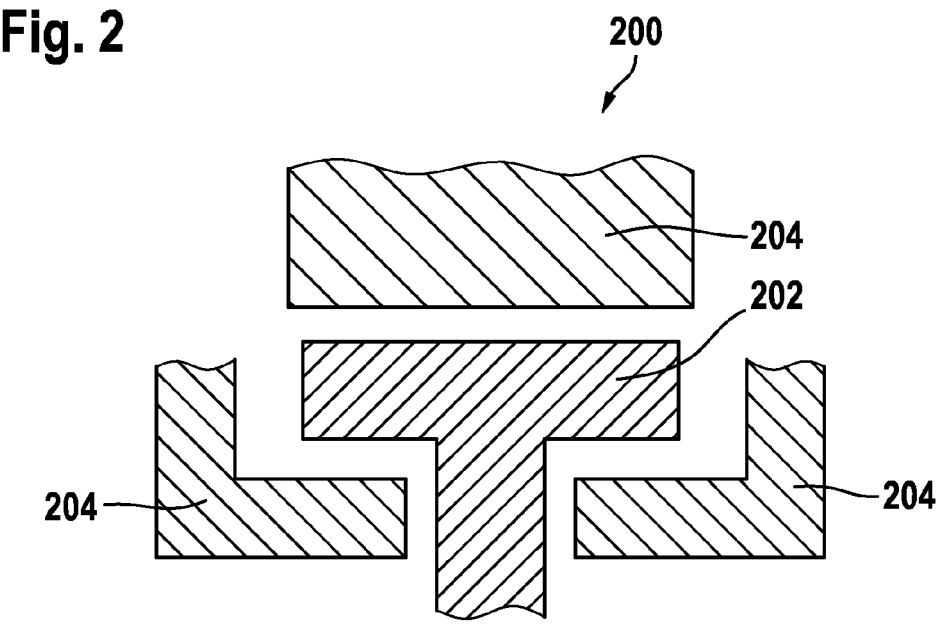
FIG. 2 illustrates a cross-sectional view of a mechanical coupling between an insertion mechanism and a helper mechanism.

FIG. 2 shows a cross-sectional view of a mechanical coupling 200 between the insertion mechanism 202 and a helper mechanism 204. The insertion mechanism 202 forms a T-shaped cross section which can be snapped into the portion of the helper mechanism 204. This T-like section allows the helper mechanism 204 to both push and pull the insertion mechanism 202 to actuate it.

Figure 3:
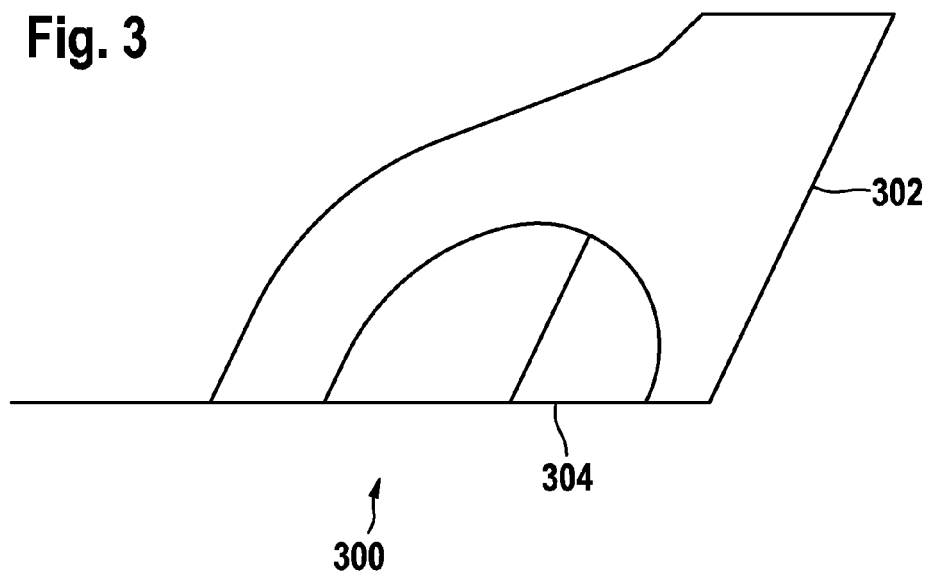
FIG. 3 illustrates an inserter assembly.

FIG. 3 shows an inserter assembly 300. The inserter assembly 300 comprises an inserter 302 and a sensor mounting unit 304. The sensor mounting unit 304 comprises the sterile capsule and can be removed from the inserter 302. When the insertion needle is used the sensor mounting unit 304 is released from the inserter 302. Additionally, in some examples the insertion mechanism may cause the insertion needle to withdraw back into the sterile capsule after insertions. This may have the advantage that the formerly sterile capsule provides protection to the used insertion needle.

Figure 4:
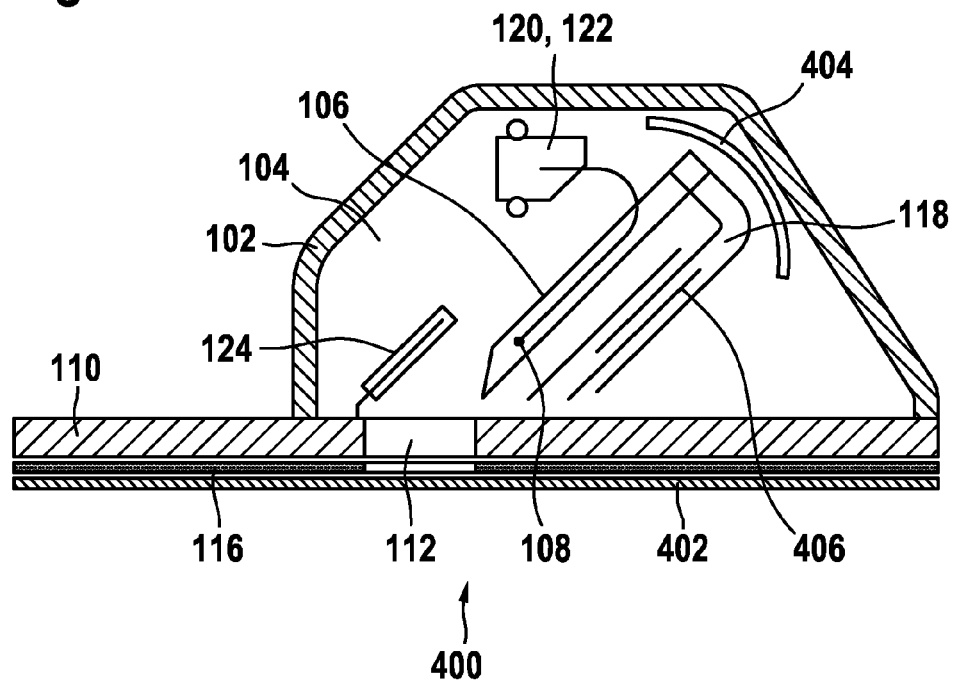
FIG. 4 illustrates a sensor cartridge according to a further example.

FIG. 4 shows a further example of a sensor cartridge 400 according to this disclosure. The example shown in FIG. 4 is similar to that shown in FIG. 1 with several structural differences. In this example there is a cover 402 covering the adhesive surface and the hole 112. Additionally this sensor cartridge 400 is intended to be operated manually and not by a helper mechanism or actuating mechanism of some sort. There is a pushing surface 404 within the sterile capsule 104. The subject can push on the package 102 and depress the pushing surface 404. The insertion mechanism 118 comprises a guide 406 or slide, which is used to control the orientation and of the insertion needle 106. During use the subject would take the cover 402 off and adhere the sensor mounting unit 110 to another surface such as the stomach. The subject would then press on the package 102 depressing the area of the pushing surface 404. This would cause the insertion needle 106 to be guided by the guide 406 and enter the subject. When the subject stops pressing on the pushing surface 404 the insertion needle 406 would retract leaving the sensor connector 120 in the mounted position 124 and the sensor 108 within the subject. In some examples, the package 102 and the insertion mechanism 118 would then detach from the sensor mounting unit 110.

FIG. 5 shows an example of a sensor cartridge according to this disclosure. The sensor cartridge 500 comprises a bellows 502. The bellows are attached to a sensor mounting unit 110. The bellows 502 and the sensor mounting unit 110 form a sterile capsule 104. Within the sterile capsule 104 is an insertion needle 106 for inserting a sensor 108. The sensor 108 is connected to a sensor mounting unit 110 which is located in an initial position 122. When a force is directed along the direction 504 the bellows is able to collapse and the insertion needle 106 is driven into the subject which causes the sensor 108 to be located within the subject and the sensor connector 120 is moved into the mounted position 124. When the force 504 is released the insertion needle 106 is retracted by the spring-like effect of the bellows 502. In some mechanisms this causes the bellows 502 to automatically detach from the sensor mounting unit 110. In other examples a connector or screw connection may be used to remove the bellows 502 from the sensor mounting unit 110.

FIG. 6 illustrates a safety 600 which may be implemented on the sensor cartridge 500 shown in FIG. 5. In this example a large wire or bar is positioned between the top of the bellows 502 and the sensor mounting unit 110. In this case it is not possible to depress the bellows.

Figure 7:
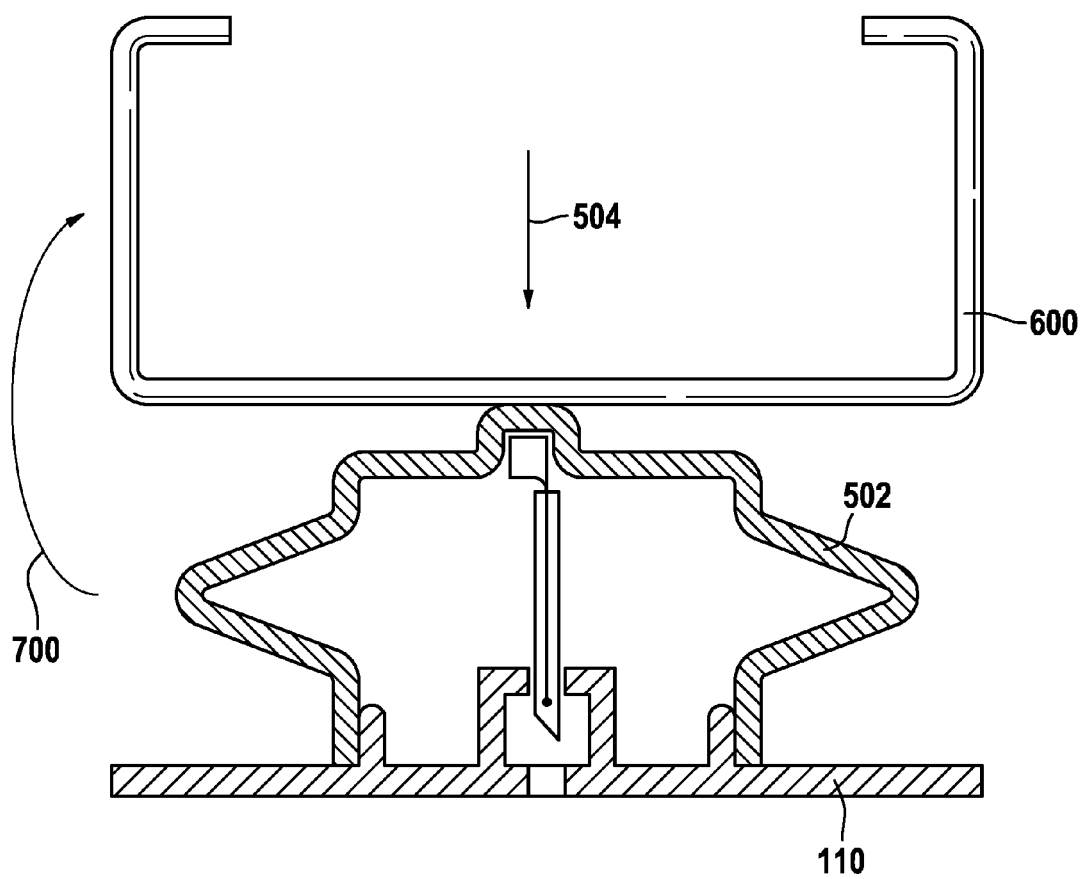
FIG. 7 illustrates the safety of FIG. 6 in an enabled position.

FIG. 7 shows the same safety 600 in an enabled position. In this example the safety 600 has been rotated 700. The safety 600 no longer prevents the bellows 502 from being depressed. In this case a force may be applied along direction 504 in order to insert the sensor into the subject.

Figure 8:
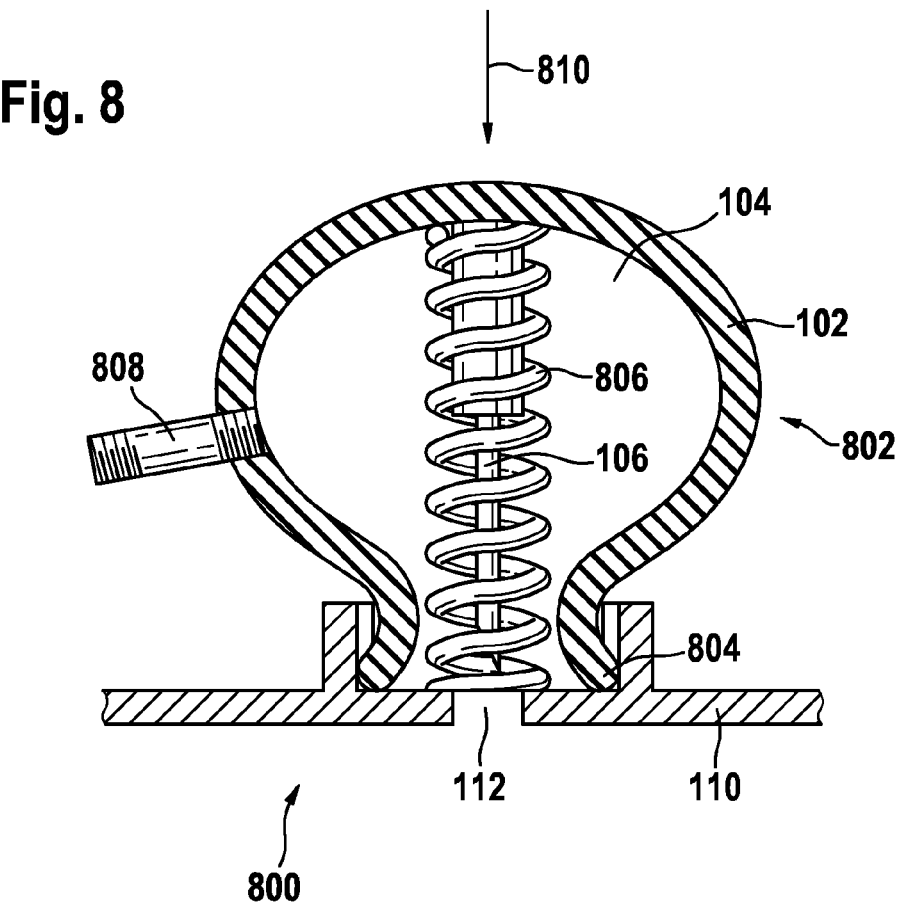
FIG. 8 illustrates a sensor cartridge according to a further example.

FIG. 8 shows a sensor cartridge 800 according to a further example of this disclosure. In this example there is a sensor mounting unit 110. Above this there is a package 102 with a flexible surface or at least partially flexible that is pressurized. This forms a sterile capsule 104 and essentially is a pressurized vessel 802. There is a seal between the package 102 and the sensor mounting unit 110. The seal is similar to that found on radial tires. The pressure maintains the force of the seal. A valve 808 is used to release pressure when a force in the direction of 810 is applied to the sensor cartridge 800. A force in the direction 810 causes the pressurized vessel 802 to gradually lose pressure as the sensor cartridge 800 is depressed. There is a spring 806 surrounding the insertion needle 106. Insertion needle 106 goes through the hole 112. In some examples there may be a septum present to maintain the pressure of the pressurized vessel 802. The spring 806 will return the insertion needle 106 to its original starting position after the force in the direction 810 is released. After the insertion needle 106 has been inserted the pressure in the pressurized vessel 802 is lower and the seal 804 may no longer function. This may cause the entire package 102 to release from the base plate 110.

Figure 9:
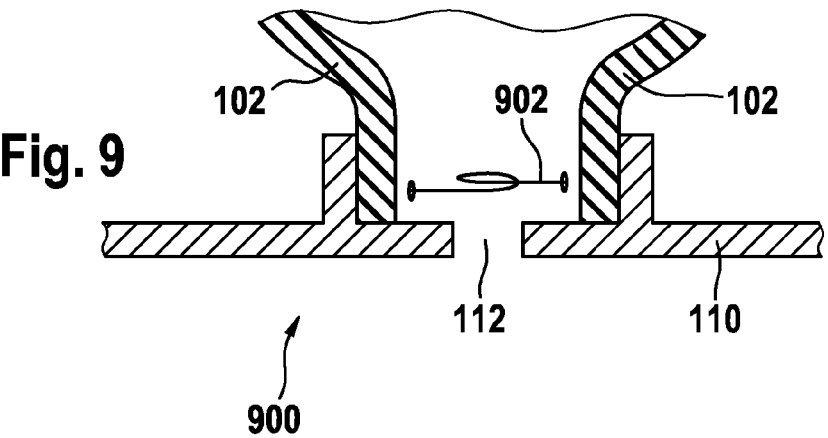
FIG. 9 illustrates a sensor cartridge according to a further example.

FIG. 9 shows a further example of a sensor cartridge 900 according to this disclosure. Only a portion of the example in FIG. 9 is shown. The example shown in FIG. 9 is equivalent to that shown in FIG. 8 except a pressurized vessel is not used to maintain a contact between the package 102 and the base plate 110. In this example there is a spring retainer ring 902 which holds the package 102 to the base plate 110. When the insertion needle is retracted the spring 902 is released and the package or cover 102 is freely removed from the base plate 110.

Figure 10:
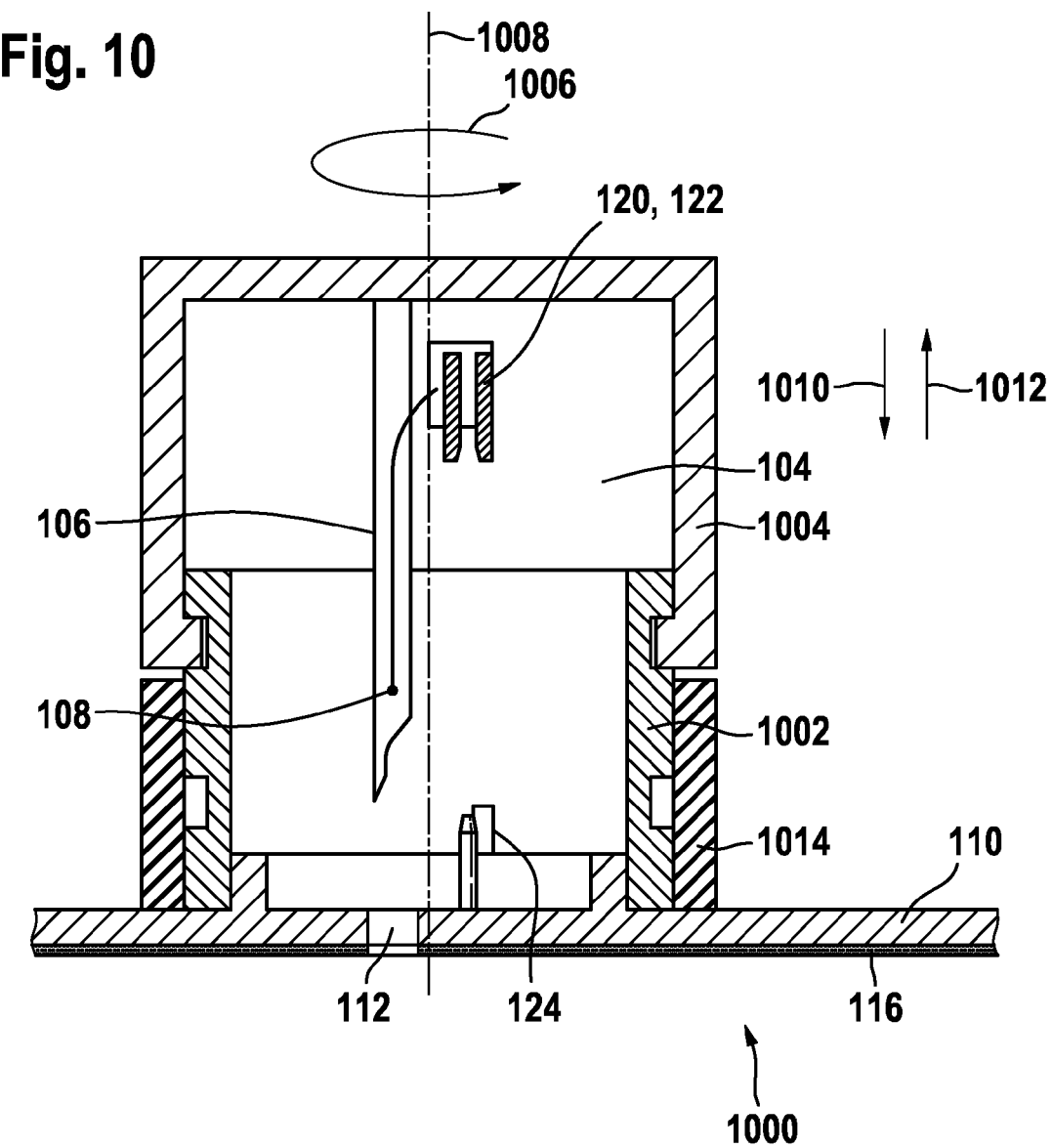
FIG. 10 illustrates a sensor cartridge according to a further example.

FIG. 10 shows an example of a sensor cartridge 1000 according to an example. In this example a cylindrical gear 1002 and a knob 1004 form the sterile capsule 104. The knob 1004 is operable for driving along the cylindrical gear 1002. When the knob 1006 is rotated in the direction 1006 about the axis of rotation 1008 the insertion needle 106 moves in the direction 110. In some examples the gear 1002 is shaped such that as the knob is continually rotated in direction 1006 the insertion needle 106 reaches its apex of insertion and then begins to go back in the retraction direction 1012. In other examples the subject rotates the knob 1004 as far as possible and then after reaching a stopping point the subject rotates the knob in the direction opposite to 1006 to go back in the direction 1012. The gear 1002 is attached to the sensor mounting unit 110. Also shown is an optional protector 1014 which protects the surface or grooves of the cylindrical gear 1002. If the protector 1014 is not present in some examples, in other examples the protector 1014 is collapsible or crushable. In other examples the protector 1014 falls or is torn off as the knob 1004 is turned.

Figure 11:
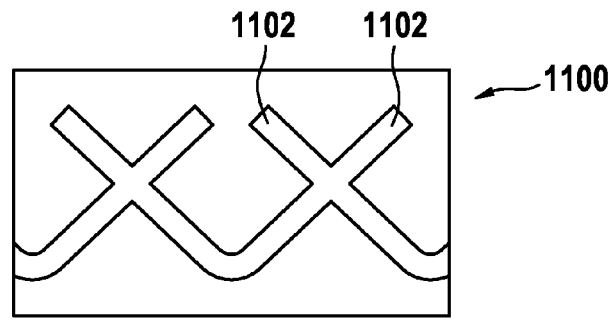
FIG. 11 illustrates a gear pattern which may be used for the cylindrical gear in FIG. 10.

FIG. 11 shows a gear pattern 1100 which may be used for the cylindrical gear 1002. The example 1100 is a gear with two slots 1102. The gear pattern 1100 is wrapped around a cylinder. Guides which control the depth of the insertion needle may be positioned in each of the slots. As the cylinder is rotated or as the guides are rotated relative to the cylinder the guides follow the slots. This causes the insertion needle to first travel into the subject and then to be retracted from the subject. With a single rotational motion, the insertion needle is inserted and retracted.

Figure 12:
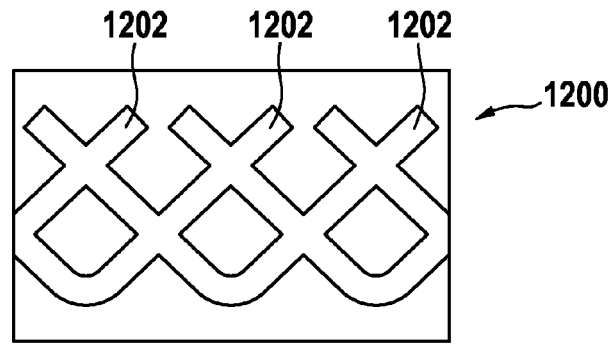
FIG. 12 illustrates an alternative gear pattern which may be used for the cylindrical gear in FIG. 10.

FIG. 12 shows a different gear pattern with three slots 1103 instead of two as was shown in FIG. 11. The gear pattern 1200 is wrapped around a cylinder. Guides which control the depth of the insertion needle may be positioned in each of the slots. As the cylinder is rotated or as the guides are rotated relative to the cylinder the guides follow the slots. This causes the insertion needle to first travel into the subject and then to be retracted from the subject. With a single rotational motion, the insertion needle is inserted and retracted.

Figure 13:
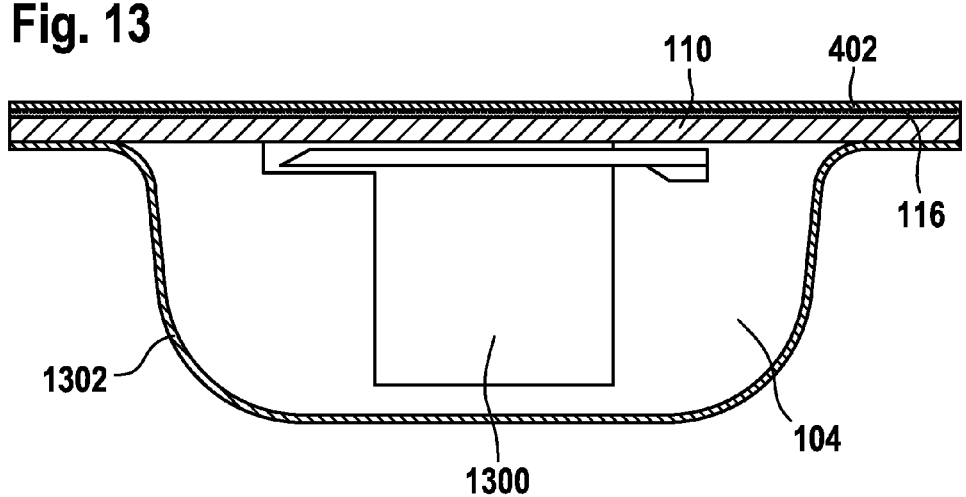
FIG. 13 illustrates a sensor cartridge according to a further example.

FIG. 13 shows a sensor cartridge 1300 according to an example. In this example the blister packaging 1302 or retail packaging forms the sterile capsule 104 with the sensor mounting unit 110. There is a cover 402 over the adhesive surface 116. The sensor cartridge 1300 is removed from the packaging 1302 by removing the cover 402 and placing the adhesive surface 116 on the surface of the subject. This example may have the advantage that reduces the amount of waste which is produced and may also reduce the manufacturing cost as the packaging of the product is incorporated into forming the sterile capsule 104.

Figure 14:
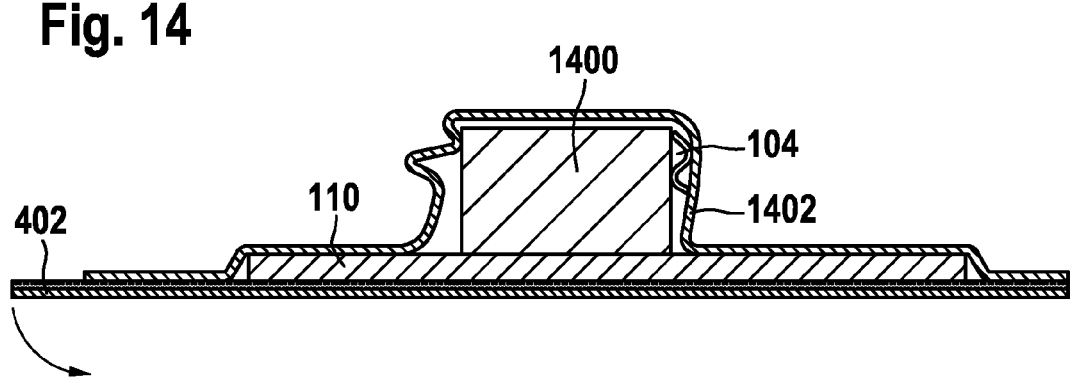
FIG. 14 illustrates a sensor cartridge according to a further example.

FIG. 14 shows an example similar as shown in FIG. 13. However in this example there is a sensor cartridge 1400 covered by a blister packaging 1402 which is again sealed by a cover 402 in the same fashion as shown in FIG. 13 except in this case the sterile capsule 104 is just bigger than the sensor cartridge 1400. This example may have several advantages. First, the surface surrounding the sensor cartridge 1400 may be easier for a subject to grab. Additionally, the cartridge can be inserted into a system which punctures the packaging 1402 and enables it to actuate the insertion mechanism within the sensor cartridge 1400.

Figure 15:
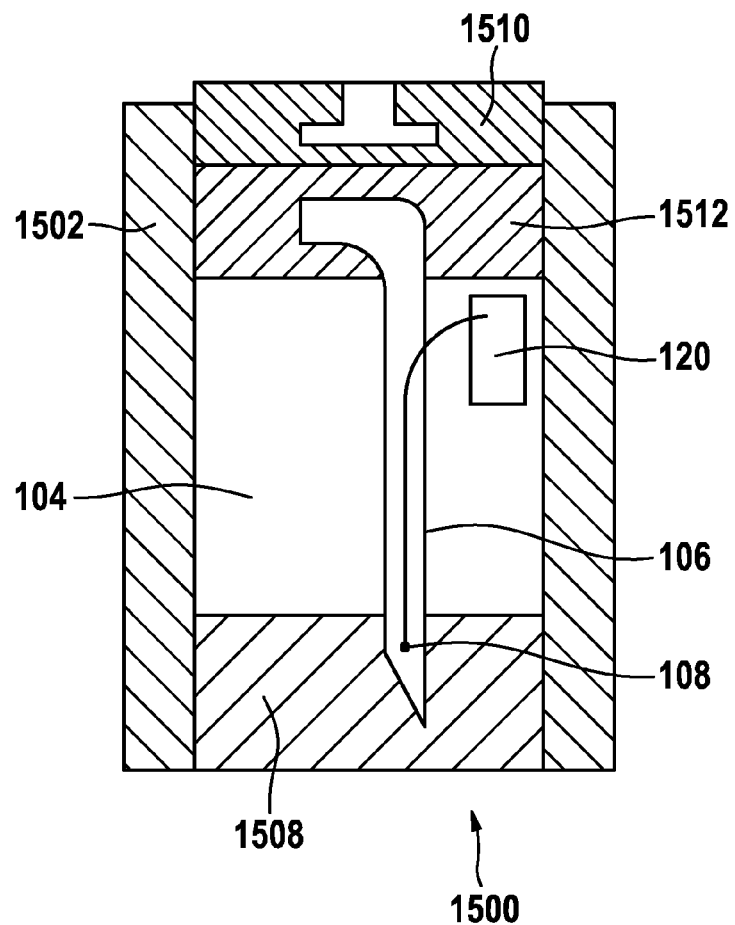
FIG. 15 illustrates a sensor cartridge according to a further example.

FIG. 15 shows a sensor cartridge 1500 according to an example. The sensor cartridge 1500 is formed by a tube 1502 which forms a sterile capsule or hollow cavity 1504. On one end a septum 1508 seals the tube 1502. On the other end a mechanical actuator or adapter 1510 is in contact with a top seal 1512. The mechanical adapter 1510 can be used to drive an insertion needle 106 through the septum 1508 and also retract it. There is also a sensor 108 within the sterile capsule 1504. In this arrangement, the septum seals the sterile capsule until the insertion needle pierces it. The septum functions as a seal that is automatically opened only at the moment of inserting the insertion needle. The seal is not opened before this.

Figure 16:
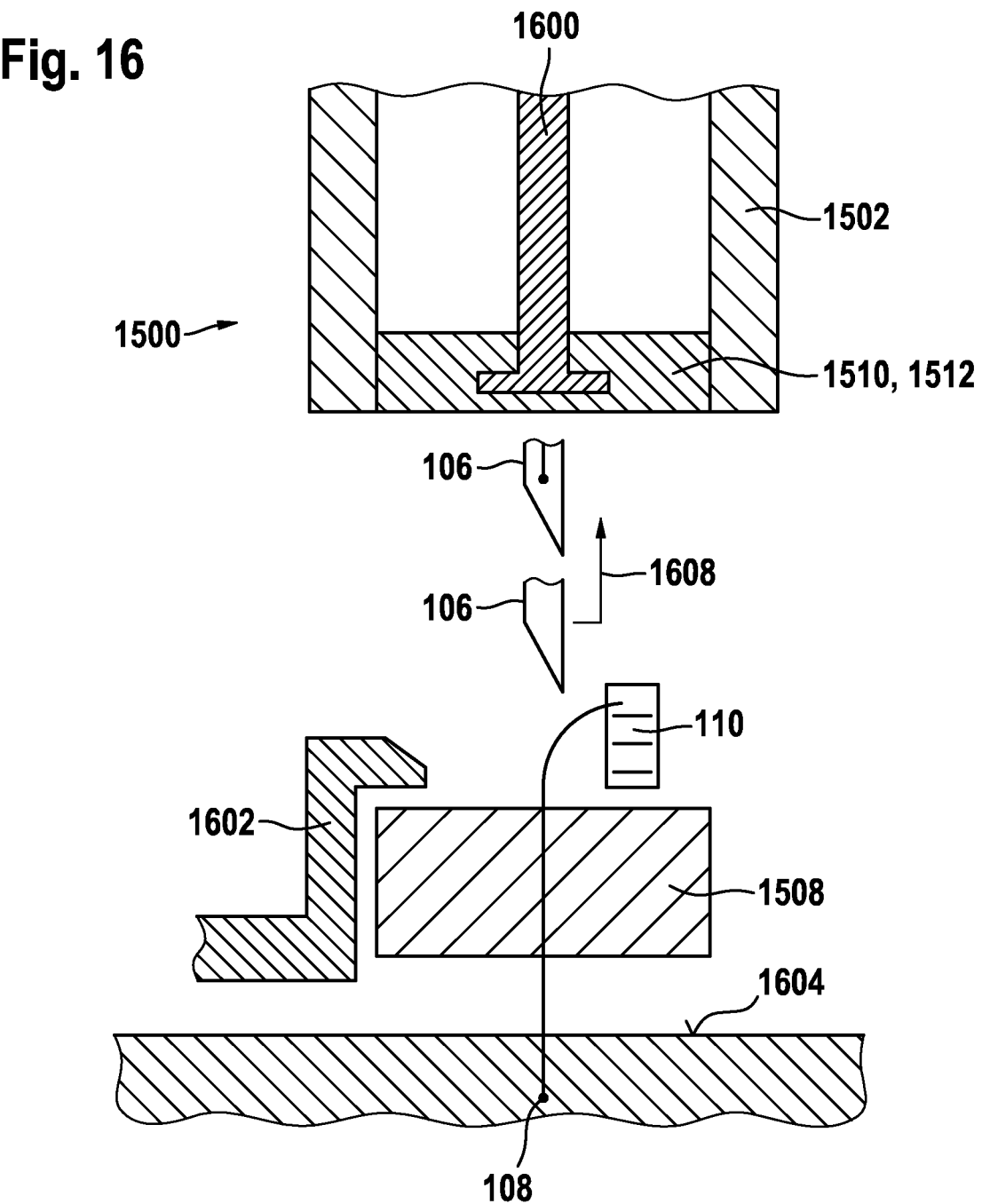
FIG. 16 illustrates the operation of the sensor cartridge shown in FIG. 15.

FIG. 16 illustrates the operation of the sensor cartridge 1500 as shown in FIG. 15. A portion of an insertion mechanism 1600 is shown as being attached to the mechanical adapter 1510. The mechanical adapter has been used to drive the insertion needle 106 through the surface 1604 of a subject. A sensor mounting unit 1602 is attached to the surface of the subject 1604. A sensor 108 has been inserted into the subject and the electrical connection 112 goes back to the sensor connector 110. The septum 1508 is left in place and is connected to the sensor mounting unit 1602. The insertion needle 106 is withdrawn 1608. The retraction of the insertion mechanism 1600 causes the insertion needle 106 to be withdrawn back into the tube 1502.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMERALS

| | |
|---|---|
| 100 | sensor cartridge |
| 102 | package |
| 104 | sterile capsule |
| 106 | insertion needle |
| 108 | sensor |
| 110 | sensor mounting unit |
| 112 | hole |
| 114 | subject |
| 116 | adhesive surface |
| 118 | insertion mechanism |
| 120 | sensor connector |
| 122 | initial position |
| 124 | mounted position |
| 200 | mechanism coupling |
| 202 | insertion mechanism |
| 204 | helper mechanism |
| 300 | inserter assembly |
| 302 | inserter |
| 304 | sensor mounting unit |
| 400 | sensor cartridge |
| 402 | cover |
| 404 | pushing surface |
| 406 | guide |
| 500 | sensor cartridge |
| 502 | bellows |
| 504 | direction of force |
| 600 | safety |
| 700 | rotation |
| 800 | sensor cartridge |
| 802 | pressurized vessel |
| 804 | seal |
| 806 | spring |
| 808 | valve |
| 810 | direction of force |
| 900 | sensor cartridge |
| 902 | spring clip |
| 1000 | sensor cartridge |
| 1002 | gear |
| 1004 | knob |
| 1006 | direction of rotation |
| 1008 | axis of rotation |
| 1010 | insertion direction |
| 1012 | retraction direction |
| 1014 | protector |
| 1100 | gear pattern |

-continued

LIST OF REFERENCE NUMERALS

| | |
|---|---|
| 1102 | slot |
| 1200 | gear pattern |
| 1202 | slot |
| 1300 | sensor cartridge |
| 1302 | blister packaging |
| 1400 | sensor cartridge |
| 1402 | blister packaging |
| 1500 | sensor cartridge |
| 1502 | tube |
| 1504 | sterile capsule or hollow cavity |
| 1508 | septum |
| 1510 | mechanical adaptor or piston |
| 1512 | top seal |
| 1600 | insertion mechanism |
| 1602 | sensor mounting unit |
| 1604 | surface of subject |
| 1608 | retraction of insertion needle |

The invention claimed is:

1. A sensor cartridge, comprising:
a sterile capsule;
a sensor located within the sterile capsule;
a sensor connector connected to the sensor in an initial position;
an insertion needle located within the sterile capsule and adapted for inserting the sensor into a subject, wherein the sensor is located within the insertion needle;
a sensor mounting unit for locking the sensor connector at a mounted position, the sensor mounting unit forming a bottom portion of the sterile capsule and comprising an adhesive surface configured for attaching to an exterior surface of the subject, wherein the sensor mounting unit is operable for receiving the sensor connector at the mounted position; and
an actuator operable for actuating the insertion needle and for withdrawing the needle, wherein the actuating of the insertion needle moves the sensor connector from the initial position to the mounted position, thereby leaving the sensor within the subject, wherein the moving of the sensor connector from the initial position to the mounted position locks the sensor connector in the mounted position.

2. The sensor cartridge of claim 1, wherein the sensor cartridge further comprises a knob, wherein the actuator is operable for actuating the insertion needle in a linear direction upon rotation of the knob.

3. The sensor cartridge of claim 1, wherein the sensor mounting unit is detachably connected to the actuator and the actuator is operable for detaching the sensor mounting unit from the actuator at a predetermined point in the actuation of the insertion needle.

4. The sensor cartridge of claim 1, wherein the sterile capsule comprises a pressurized vessel, wherein a pressure differential between the pressurized vessel and outside the sensor cartridge causes the attachment of the actuator to the mounting unit, the sensor cartridge further comprising a seal and/or valve for maintaining the pressure differential, wherein the actuator is configured to cause the seal and/or valve to release the pressure differential during actuation of the actuator.

5. The sensor cartridge of claim 1, wherein:
the sterile capsule is a hollow cavity;
the actuator comprises a piston and is operable for pushing the piston into the hollow cavity for driving the insertion needle into the subject;

the actuator is further operable for retracting the insertion needle back into the hollow cavity after insertion of the sensor into the subject using the piston.

6. The sensor cartridge of claim 1, wherein the actuator comprises a safety which is movable from an operable position to an inoperable position, and wherein the actuator prevents actuation of the needle when the safety is in the inoperable position and enables actuation of the needle when the safety is in the operable position.

7. The sensor cartridge of claim 1, wherein the actuator is configured to couple to a helper mechanism of an inserter, wherein the helper mechanism is operable for actuating the actuator.

8. The sensor cartridge of claim 1, wherein the actuator is further operable for retracting the insertion needle into the sterile capsule after actuating the insertion needle and moving the sensor from the initial position to the mounted position.

9. A sensor cartridge, comprising:
a sterile capsule;
a sensor located within the sterile capsule;
a sensor connector connected to the sensor in an initial position;
an insertion needle located within the sterile capsule and adapted for inserting the sensor into a subject, wherein the sensor is located within the insertion needle;
a sensor mounting unit for locking the sensor connector at a mounted position, the sensor mounting unit forming a bottom portion of the sterile capsule and comprising an adhesive surface configured for attaching to an exterior surface of the subject, wherein the sensor mounting unit is operable for receiving the sensor connector at the mounted position; and
an actuator operable for actuating the insertion needle and moving the sensor connector from the initial position to the mounted position and for withdrawing the needle, thereby leaving the sensor within the subject, wherein the moving of the sensor connector from the initial position to the mounted position during the actuating of the insertion needle locks the sensor connector in the mounted position.

* * * * *